US007144723B2

(12) United States Patent
Fenical et al.

(10) Patent No.: US 7,144,723 B2
(45) Date of Patent: Dec. 5, 2006

(54) MARINE ACTINOMYCETE TAXON FOR DRUG AND FERMENTATION PRODUCT DISCOVERY

(75) Inventors: William Fenical, Del Mar, CA (US); Paul R. Jensen, San Diego, CA (US); Tracy J. Mincer, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/991,518

(22) Filed: Nov. 16, 2001

(65) Prior Publication Data

US 2003/0157695 A1 Aug. 21, 2003

Related U.S. Application Data

(60) Provisional application No. 60/249,356, filed on Nov. 16, 2000.

(51) Int. Cl.
*C12N 1/20* (2006.01)
(52) U.S. Cl. .................... 435/252.1; 424/93.4
(58) Field of Classification Search ............. 435/252.1, 435/41, 71.2, 72, 106, 117, 128, 170
See application file for complete search history.

(56) References Cited

U.S. PATENT DOCUMENTS

| | | | |
|---|---|---|---|
| 5,756,764 A | 5/1998 | Fenteany et al. | |
| 6,133,308 A | 10/2000 | Soucy et al. | |
| 6,147,223 A | 11/2000 | Fenteany et al. | |
| 6,214,862 B1 | 4/2001 | Fenteany et al. | |
| 6,294,560 B1 | 9/2001 | Soucy et al. | |
| 6,335,358 B1 | 1/2002 | Fenteany et al. | |
| 6,458,825 B1 | 10/2002 | Fenteany et al. | |
| 6,566,553 B1 | 5/2003 | Soucy et al. | |
| 6,645,999 B1 | 11/2003 | Schreiber et al. | |
| 6,794,516 B1 | 9/2004 | Soucy et al. | |
| 6,838,477 B1 | 1/2005 | Schreiber et al. | |
| 6,849,743 B1 | 2/2005 | Soucy et al. | |
| 2001/0002391 A1 | 5/2001 | Brand et al. | |
| 2001/0051654 A1 | 12/2001 | Elliott et al. | |
| 2004/0138196 A1 | 7/2004 | Fenical et al. | .............. 514/192 |

FOREIGN PATENT DOCUMENTS

| | | |
|---|---|---|
| WO | WO 96/32105 | 10/1996 |
| WO | WO96/32105 | 10/1996 |
| WO | WO 99/09006 | 2/1999 |
| WO | WO00/23614 | 4/2000 |
| WO | WO/02/47610 | 6/2002 |
| WO | WO 02/47610 A2 | 6/2002 |
| WO | WO/2004/071382 | 8/2004 |
| WO | WO 2004/071382 A2 | 8/2004 |
| WO | WO/2005003137 | 1/2005 |

OTHER PUBLICATIONS

Bull, A. T. et al. 2000. Search and discovery strategies for biotechnology: The paradigm shift. Microbiology and Molecular Biology Reviews. 64:573-606.
Goodfellow, M. et al. 1984. Actinomycetes in marine sediments, p. 453-472. Biological, biochemical, and biomedical aspects of actinomycetes. Academic Press, Inc. Orlando.
Goodfellow, M. et al. 1983. Ecology of actinomycetes. Ann. Rev. Microbiol. 37:189-216.
Helmke, E. et al. 1984. *Rhodococcus marinonascens* sp. nov., an actinomycete from the sea. Int. J. Syst. Bacteriol. 34:127-38.
Hopwood, D.A. 1995. Genetic manipulation of streptomyces polyketide synthase genes for novel secondary metabolite production. FEMS Microbiol. Rev. 16:233-4.
Jensen, P.R., et al. 1991. Distribution of actinomycetes in near-shore tropical marine sediments. Appl. Environ. Microbiol 57:1102-8.
Koch, C., et al. 1996. 16S ribosomal DNA analysis of the genera Micromonospora, Actinoplanes, . . . Int. Journal of Systematic Bacteriology. 46:765-768.
Moran, M.A. et al. 1995. Evidence for indigenous streptomyces populations in a marine environment . . . , pp. 3695-3700. Applied and Environmental Microbiology. vol. 61, No. 10.
Nesternenko, O.A., et al. 1982 *Rhodococcus luteus* nom. nov. and *Rhodococcus maris* nom. nov. pp. 1-14. Int'l Journal of Systematic Bacteriology. vol. 32, No. 1.
Nolan, R.D. et al. 1988. Isolation and screening of actinomycetes, pp. 1-32. Actinomycetes in Biotechnology.
O'Donnell, A.G. 1988. Recognition of novel actinomycetes, pp. 69-88. Actinomycetes in Biotechnology.
Okami, Y. et al. 1988. Search and discovery of new antibiotics,pp. 33-67. Actinomyetes in Biotechnology.
Page, R. D. M. 1996. TREEVIEW: An application to display phylogenetic trees on personal computers. Computer Applications in the Biosciences 12, 357-358.
Stackebrandt, E. et al. 1997. Proposal for a new hierarchic classification system, Actinobacteria classis nov. International Journal of Systematic Bacteriology. 47:479-491.
Tang, L. et al. 2000. Cloning and heterologous expression of the epothilong gene cluster. Science. 287:640-2.
Thompson, J.D. et al. 1994. CLUSTAL W: Improving the sensitivity of progressive multiple sequence alignment through sequence weighting, . . . Nucleic Acids Research 22:4673-4680.
Versalovic, J. et al. 1991. Distribution of repetitive DNA sequences in eubacteria and application to fingerprinting of bacterial genomes. Nucleic Acids Res. 19:6823-6831.
Weyland, H. 1981. Distribution of actinomycetes on the sea floor. Actinomycetes, Zbl. Bakt. Suppl. 11:185-193.

(Continued)

*Primary Examiner*—Irene Marx
(74) *Attorney, Agent, or Firm*—DLA Piper Rudnick Gray Cary US LLP

(57) ABSTRACT

The invention is the discovery of an actinomycete genus, given the name *Salinospora* gen. nov., that displays an obligate requirement of seawater ($Na^+$) for growth and unique 16S rRNA signature nucleotides. The invention is also the use of the genus for the production and discovery of active biomolecules such as pharmaceutical agents, agrichemicals, immunomodifiers, enzymes and enzyme inhibitors.

9 Claims, 2 Drawing Sheets

OTHER PUBLICATIONS

Hardt et al., "Neomarinone, and new cytotoxic marinone derivatives, produced by a marine filamentous bacterium (actinomycetales)", *Tetrahedron Letters*, Mar. 2000, 41(13):2073-6.

Jensen et al., "The Relative Abundance and Seawater Requirements of Gram-Positive Bacteria in Near-Shore Tropical Marine Samples", *Microb Ecol.*, 1995, 29(3):249-57.

Jiang et al., "Actinoflavoside, A Novel Flavonoid-Like Glycoside Produced by a Marine Bacterium of the Genus *Streptomyces*", *Tetrahedron Letters*, 38(29):5065-8.

Feling et al., Angew. (2003) Angew. Chem. Int. Ed. 42(3):355-357.

Fusetani (ed.): *Drugs from the Sea*. Basel, Karger 2000, pp. 6-29.

Davidson, B.S., Current Opinion in Biotechnology 1995, 6:284-291.

Blunt, J.W., et al., Nat. Prod. Rep., 2003, 20:1-48.

Colquhoun, J.A., et al., Extremophiles, 1998, 2:269-277.

Fenical, W., Chem. Rev. 1993, 93:1673-1683.

Fenical, W., Marine Biotechnology 1997, 15:339-341.

Fernandez-Chimeno R.I., et al., Journal of Antibiotics, 2000 53(5):474-478.

Goodfellow and O'Donnell, (1989) Search and discovery of industrially significant actinomycetes. In *Microbial Products: New Approaches, Society for General Microbiology Symposium No. 44* eds Baumberg, S., et al., pp. 343-383. Cambridge: Cambridge University Press.

Horan, A.C. "Aerobic Actinomycetes: A Continuing Source of Novel Natural Products." In Gullo, V.P. (ed.), *The Discovery of Natural Products with Therapeutic Potential*. Boston: Butterworth-Heinemann, 1994, pp. 1-30.

Romero, F., et al., The Journal of Antibiotics, 1997, 50(9):734-737.

Watve, M.G. et al., 2001, Arch. Microbiol 176:386-390.

Weyland, J., Nature, 1969, 223:858.

Zheng, Z, et al., FEMS Microbiology Letters, 2000, 188:87-91.

Mincer, T.J., et al., Appl. Environ. Microbiol., 2002, 68(10):5005-5011.

He, H., et al., J. Am. Chem. Soc., 2001, 123:5362-5363.

Stach, J.E.M., et al., Appl. Environ. Microbiol., 2003, 69(10):6189-6200.

Colquhoun, J.A., et al., Antonie van Leeuwenhoek, 1998, 74:27-40.

Stach, J.E.M. et al., Envion. Microbiol., 2003, 5(10):828-841.

Elliott, P.J. et al., J. Mol. Med., 2003, 81:235-245/.

Joseph, S.J., et al., 2003, Appl Environ. Microbiol. 69(12):7210-7215.

Otoguro, M., et al., J. Appl. Microbiol., 2001, 92:118-130.

Cheng, X.C., et al., J. Nat. Prod., 1999, 62:608-610.

Cheng, X.C., et al., J. Nat. Prod. 1999, 62:605-607.

Erba, E., et al., British Journal of Cancer, 1999, 88(7):971-980.

Beman, V.S., et al., Advances in Applied Microbiology 1997, 43:57-90.

Jenson and Fenical, Annu. Rev. Microbiol 1994, 48:559-84.

Okami, Y., Journal of Marine Biotechnology 1993, 1:59-65.

Goodfellow and O'Donnell, (1988) "Actinomycetes in Biotechnology", Okami, et al., ed., *Search and Discovery of New Antibiotics*. Academic Press: San Diego 1988, pp. 33-67.

Beers, et al., "The Merck Manual of Diagnosis & Therapy" Seventeenth Edition, Merck Research Lab. pp. 1157, col. 2, p. 1158 col. 2, p. 1241, col. 2, p. 1252, col. 1, Whitehouse Station NJ (1999).

Crane, et al., "A Novel Enantioselective Synthetic Route to Omuralide Analogues with te Potential for Species Selectivity in Proteasome Inhibition", Organic Letters 3(9):1395-1397 (2001).

DeLong, et. al., "Environmental Diversity of Bacteria and Archaea", *Syst. Biol.* 50(4):470-478, (2001).

Elliott, et al., "The proteasome: A new Target for Novel Drug Therapies", Am. J. of Clin Pathology. 116(5):637-646 (2001).

Feling, et al., "Salinospormide A: A Highly Cytotoxic Proteasome Inhibitor from a Novel Microbial Source, A Marine Bacterium of the New Genus *Salinospora*" Angewandte Chemie (Intl. ed. In English), 2003 pp. 355-357.

Fenical, et al., "Marine Microorganisms as a Developing Resource for Drug Discovery", *Pharmaceutical News*, 9/6, 489-494 (2002).

Gantt, et al., "proteasome Inhibitors Block Development of Plasmodium Spp", Antimicrobial Agents and Chemotherapy 42(10):2731-2738 (1998).

Giovannoni, Steven, "Oceans of Bacteria", *Nature* 430:515-516, (Jul. 29, 2004).

Goldberg, et al., "Not Just Research Tools-proteasome Inhibitors Offer Therapeutic Promise", *Nature Medicine*, 8(4):338-340 (2002).

Newton, "Il Fondo Agli Oceani Potenti Antibiotici e Anticancro" XP002304843 Abstract-English.

Nicholas, B.J.R., "Symbiotic Approach to Drug Design" *Decision in Drug Design*, 173-186 (1983).

Rajender, et al., "A Simple Stereocontrolled Synthesis of Salinospramide A" *J. Am. Chem Soc.* 126(20):6230 (Apr. 2004).

Rappe, et al., "Cultivation of the Ubiquitous SAR11 Marine Bacterioplankton Clade," *Nature* 418:630-633, (Aug. 8, 2002).

Stackebrandt, et al., "Proposal for a New Hierarchic Classification System," *Intl. J. of Systematic Bacteriology* 47(2):479-490 (1997).

Tang, et al., "Proteasome Activity is Required for Anthrax Lethal Toxin to Kill Macrophages", Infection & Immunity 67(6):3055-3060 (Jun. 1999).

Ward, Bess, "How Many Species of *Prokaryotes* Are There?" *PNAS* 99(16):10234-10236 (Aug. 6, 2002).

Wheelis, et al., "On the Nature of Global Classification", *PNAS* 89:2930-2934, (Apr. 1992).

Woese, Carl, "Bacterial Evolution", *Microbiological Rev.* 51(2):221-271 (Jun. 1987).

Robert H. Feling et al., "Salinosporamide A: A Highly Cytotoxic Proteasome Inhibitor from a Noval Microbial Source, a Marine Bacterium of the New Genus *Salinospora*", Angew. Chem. Int. Ed. 2003, 42, No. 3, pp. 355-357.

William Fenical et al., "Marine Microorganisms as a Developing Resource for Drug Discovery", Pharmaceutical News (2002), vol. 9, pp. 489-494.

Alfred L. Goldberg et al., "Not just research tools—proteasome inhibitors offer therapeutic promise", Nature Medicine, vol. 8, No. 4, Apr. 2002, pp. 338-340.

B.J.R. Nicolaus, "Symbiotic Approach to Drug Design", Decision Making in Drug Research, 1983, pp. 173-186.

Leleti Rajender Reddy et al., "A Simple Sterocontrolled Synthesis of Salinosporamide A", J. Am. Chem. Soc., 2004, vol. 126, pp. 6230-6231.

MARINE ACTINOMYCETE TAXON FOR DRUG AND FERMENTATION PRODUCT DISCOVERY

CROSS-REFERENCES TO RELATED APPLICATIONS

This application claims the benefit of priority of U.S. provisional application Ser. No. 60/249,356 filed Nov. 16, 2000 which is incorporated herein by reference in its entirety.

GRANT INFORMATION

This invention was made with government support under Grant No. CHE-9807098 awarded by National Science Foundation. The United States government has certain fights in this invention.

FIELD OF THE INVENTION

The invention relates to the discovery of a novel taxon of marine bacteria of the order Actinomycetales and the use of this taxon for the discovery and production of proteins, secondary metabolites and biomolecules for use as pharmaceutical compositions, agrichemicals, immunomodifiers, enzymes and enzyme inhibitors.

BACKGROUND OF THE INVENTION

Microorganisms belonging to the class Actinobacteria, commonly called actinomycetes, reside taxonomically within the Gram-positive bacteria and are ubiquitous in terrestrial environments. Actinomycetes are a prolific source of diverse biologically active metabolites. They have been a source of a numerous useful products including pharmaceuticals, agrichemicals, low molecular weight enzyme inhibitors, immunomodifiers, and enzymes for use in a number of industrial applications, from the food industry to paper making. These microorganisms have also been useful in agriculture as a means of pathogen protection and growth enhancement. Although many useful substances have been discovered from soil actinomycetes over the last 60 years, the yield of novel products has drastically decreased as common soil species continually yield previously discovered metabolites. For this reason, there has been a major effort to discover new actinomycete taxa in the hope that these microorganisms will provide a new source of useful products (Bull et al., 2000).

Actinobacteria are one of a number of classes of bacteria. The class Actinobacteria can be further subdivided into six orders, including the Actinomycetales which can be broken down into 10 suborders. Classical methods for determining taxonomic novelty include morphological and physiological criteria such as color, presence or absence of mycelia, hyphal branch characteristics, spore pattern and motility, tolerance of variation in temperature, salinity and pH, and the ability to utilize various substrates. Although these criteria remain an important component of taxonomic analyses, a new and more definitive method to establish strain uniqueness is 16S rDNA sequence analysis, which also provides evolutionary information on the isolate (Stackebrandt, et al., 1997).

Membership of a strain within the class Actinobacteria is indicated by 16S rDNA sequence similarity values above 80%, as determined by comparison of almost complete 16S rDNA sequences with the most deeply branching members of the class, and the presence of signature nucleotides (Stackebrandt, 1997). Signature nucleotides specific for a taxonomic group are chosen for their presence in more than 95% of the members of that group. 16S signature nucleotide sequences can be used on various taxonomic levels, from defining an order of bacteria to the subdivision of families into genera. This method provides a powerful mathematical model of bacterial evolution and an objective, rather than subjective, set of rules by which bacteria may be assigned a taxonomic status within the classification system.

Despite the fact that the oceans cover 70% of the earth's surface, all known actinomycete genera discovered to date have been land dwellers. In fact, only one marine actinomycete species has been described (Helmke and Weyland, 1984) and it belongs to a well-known terrestrial genus. Although actinomycetes have been cultured from marine sediments, it is widely believed that marine isolates are derived from dormant terrestrial spores that were washed into the sea (Goodfellow and Haynes, 1984). The "wash-in" theory was postulated because the marine isolates did not require seawater for growth, were closely related to terrestrial species, and tended to decrease in number with increasing distance from land (Goodfellow and Williams, 1983). Because many terrestrial actinomycetes can tolerate high salinity and pressure, and because of their distribution and physiology, it was concluded that most actinomycetes have been washed into the sea and collect in sediments where they can survive for long periods of time as spores (Goodfellow and Haynes, 1984). These types of studies have led to the general belief that marine actinomycetes are not significantly different from those on land and therefore of little utility as a source of novel industrial products.

SUMMARY OF THE INVENTION

The invention is the discovery, isolation and characterization of the first major obligate marine actinomycete taxon for which the name *Salinospora* gen. nov. is proposed. Members of this genus are readily recognized by a series of characteristic features including:

1. Obligate requirement of sodium (seawater) for growth.
2. Presence of at least 4 of the 5 16S rRNA signature nucleotides (Table 3) and close phylogenetic relatedness to the *Salinospora* clade using 16S rRNA treeing methods.
3. Morphological characteristics typically including:
   a.) colony color ranging from orange to brown,
   b.) no or scant aerial mycelia,
   c.) diffusable melanin-like pigments and spores that blacken the colony surface,
   d.) hyphae that are finely branched and non-fragmenting with spores produced singly or in clusters.

Comparison with a deposit of a type strain at the ATCC (American Type Culture Collection; 12301 Parklawn Drive; Rockville, Md. 20852) on Sep. 27, 2000 under number ATCC PTA-2501.

The discovery of the *Salinospora* group refutes prior notions about actinomycetes in the marine environment and provides the first unequivocal evidence that major populations of unique, obligate marine actinomycetes occur widely in ocean sediments. Chemical studies of *Salinospora* group members have led to the isolation of novel compounds and an exceptionally high rate of biologically active extracts indicating that these microorganisms have utility for drug discovery and other industrial applications.

The invention is the use of the novel taxon for the discovery and production of proteins, secondary metabolites and other biomolecules for use in pharmaceutical compositions, agrichemicals, immunomodifiers, enzymes and enzyme inhibitors. Active molecules can be purified from the actinomycetes themselves or metabolites may be purified from the growth media. This genus is a rich source of active biomolecules with many demonstrated pharmacological activities (e.g. antifungal, antimicrobial, anti-cancer). Extracts and products can be used in a number of assays well known to those skilled in the art to determine the activity of the various compounds derived from the actinomycetes.

The invention is the use of the genome of the taxon for the production of biomolecules in the context of the endogenous actinomycete strain or in other organisms. Genes may be expressed singly or in clusters under the control of constitutive or inducible promoters. Genes from the invention may be expressed in heterologous hosts as recombinant or over producing strains. Other portions of the genome, such as transcriptional regulatory elements, can also be used in heterologous contexts for the control of transcription. The genome may be either wild-type or mutant. Mutations may be spontaneous or created in a random or site directed manner by methods well known to those skilled in the art.

The invention is the use of the taxon for the production of gene products from heterologous organisms. Genes may be inserted either singly or in clusters into the actinomycete strains of the invention for expression of proteins, secondary metabolties or other biomolecules. Compounds may be isolated from the actinomycetes or the growth media.

The invention is the use of the taxon for pathogen and pest protection, insecticides, herbicides, microbiocides, growth promotion in agriculture and aquaculture applications. Actinomycetes of the instant invention can compete with harmful micro-organisms in the environment of the plants providing a non-toxic means of protecting plants.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which.

Figure 1:
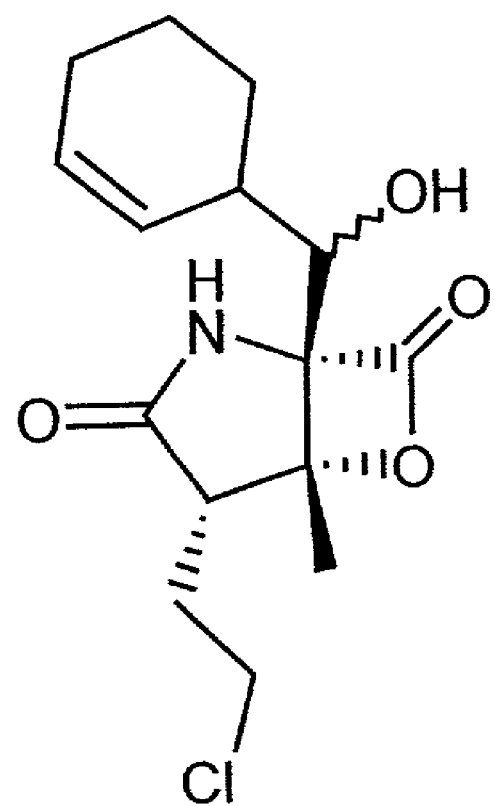
FIG. 1. Structure of salinosporamide A, the first novel, bioactive metabolite obtained from the *Salinospora* group. The isolation of this compound proves that the *Salinospora* group is a resource for unique, biologically active metabolites. The producing strain was cultured in a seawater-based medium and the compound was obtained in pure form following a series of chromatographic steps. The structure of salinosporamide A was elucidated using 1 D and 2D nuclear magnetic resonance and high resolution mass spectral data analyses.

Applicants made the following biological deposit with the American Type Culture Collection (ATCC), 10801 University Blvd., Manassas, Va. 20110-2209 USA, and International Depositary Authority (IDA) under the terms of the Budapest Treaty on the International Recognition of the Deposit of Microorganisms for the Purposes of Patent Procedure:

Definition: *Actinomycete Salinospora*, strain CNH646
ATCC No.: PTA-2501
Date of Deposit: Sep. 27, 2000 and
Definition: *Actinomycete Salinospora*, strain CNB476
ATCC No.: PTA-5275
Date of Deposit: Jun. 20, 2003

DETAILED DESCRIPTION AND PREFERRED EMBODIMENTS

*Salinospora* strains can be consistently isolated from marine sediments and are distinguished by characteristic signature nucleotides, an obligate requirement of seawater (more specifically, $Na^+$) for growth, and morphological characteristics. Isolates belonging to this group were obtained on five separate occasions from tropical to subtropical, near-shore sediments collected from the Atlantic Ocean, the Red Sea and the Sea of Cortez indicating a world-wide distribution. In these studies, a total of 147 independent sediment samples were evaluated and 51 of these yielded a total of 182 *Salinospora* isolates of which seven were subjected to in-depth physiological and phylogenetic evaluation (Table 1). Subsequently, over 1000 strains have been obtained from additional collections.

Natural location of strains. Select, diverse isolates representing over 1000 strains with *Salinospora* morphology were used for in-depth phylogenetic and physiological analyses. Nearly complete 16S rDNA sequences (>95% of the entire gene) were obtained for all strains listed. Note that CNB394 and CNB512 are marine-derived *Micromonospora* isolates and were carried through analyses to illustrate fundamental differences between *Salinospora* and *Micromonospora* genera.

TABLE 1

| Strain | Year and location | Habitat descrip. and depth | Genus |
| --- | --- | --- | --- |
| CNH643 | 1999 Bahamas, Sweetings Cay | Coarse sand, 1 m | *Salinospora* |
| CNH646 | 1999 Bahamas, Andros Island | Spur and grove, 10 m | *Salinospora* |
| CNH725 | 2000 Red Sea, Sha'b el utal | Coarse sand, 20 m | *Salinospora* |
| CNH898 | 2000 Bahamas, Little San Salvador | Coarse sand, 30 m | *Salinospora* |
| CNH964 | 2000 Sea of Cortez Caleta Partida | Coarse sand, 30 m | *Salinospora* |
| CNB440 | 1989 Bahamas, Chub Cay | Spurand grove, 20 m | *Salinospora* |
| CNB536 | 1989 Bahamas, Acklins Island | Coarse sand and seagrass, 10 m | *Salinospora* |
| CNB394 | 1989 Bahamas, Chub Cay | Coarse sand and seagrass, 1 m | *Micromonospora* |
| CNB512 | 1989 Bahamas, San Salvador Is. | Spur and grove, 30 m | *Micromonospora* |

All of the 182 *Salinospora* strains tested failed to grow on an agar medium when seawater was replaced with deionized water. Seven phylogenetically diverse strains were further characterized and shown to require sodium for growth (Table 2), a physiological characteristic commonly associated with obligate marine bacteria. Sodium requirements have been studied extensively in Gram-negative marine bacteria and are indicative of highly evolved marine adaptations such as a respiration-dependant sodium ion pump and/or a sodium dependent membrane transport mechanism. The requirement of seawater (sodium) for growth is extremely rare in Gram-positive bacteria and has never before been reported for an actinomycete with the exception of *Rhodococcus marinonascens* (Helmke and Weyland, 1984)

Assay for sodium dependent growth. Physiological growth analysis illustrating fundamental growth differences between *Salinospora* (in bold) and marine-derived *Micromonospora* isolates (CNB394, CNB512) are shown in Table 2. Tests were performed on medium M1 which was found to be optimal for the growth and maintenance of *Salinospora* and *Micromonospora* genera. Isolates were screened using a sterile cotton swab to inoculate macerated, vegetative mycelia onto each analytical medium which was then incubated at 25–28° C. for six to eight weeks. Growth was checked periodically using a Leica stereoscope at 10–64× magnification. All strains grew equally well in natural seawater (NSW) or artificial seawater (ASW Na+). No detectable growth was observed for any of the *Salinospora* isolates on M1 prepared with de-ionized water (DI). The two *Micromonospora* isolates, CNB394 and CNB512, grew better on M1 DI water than on the seawater-based medium. Sodium growth requirements were tested on M1 prepared with ASW in which all sodium sources were replaced with equimolar amounts of potassium (M1, ASW K+). The sodium concentration in seawater of salinity 35 (used for M1, NSW medium in this study) is 450 mM. In order to determine the upper limits of sodium chloride tolerance, strains were tested for growth on M1 DI water in which sodium chloride was added to yield final sodium concentrations of 600 and 1000 mM. The *Salinospora* isolates showed no growth at these elevated sodium levels whereas growth was clearly evident for the marine-derived *Micromonospora* CNB394 and CNB512.

TABLE 2

| | Isolates Tested | | | | | | | | |
|---|---|---|---|---|---|---|---|---|---|
| Medium | CNB 394 | CNB 512 | CNB 440 | CNB 536 | CNB 643 | CNH 646 | CNH 721 | CNH 898 | CNH 964 |
| M1, NSW | + | + | ++ | ++ | ++ | ++ | ++ | ++ | ++ |
| M1, DI H$_2$O | ++ | ++ | – | – | – | – | – | – | – |
| M1 ASW, Na$^+$ | + | + | ++ | ++ | ++ | ++ | ++ | ++ | ++ |
| M1 ASW K$^+$ | + | + | – | – | – | – | – | – | – |
| 600 mM [Na$^+$] | +/– | +/– | – | – | – | – | – | – | – |
| 1000 mM [Na$^+$] | +/– | +/– | – | – | – | – | – | – | – |

*Salinospora* isolates are proving to be a remarkable source of biologically active secondary metabolites. Thus far, of the 105 strains examined, 86% yielded culture extracts with significant cancer cell cytotoxicity (IC$_{50}$ values ranging from 0.004–16.4 micrograms/ml against the HCT-116 human colon carcinoma cell line). Significant antifungal and antibiotic activities have also been observed from the extracts of cultures grown under various conditions with 30% yielding MIC values of 19.5 micrograms/ml or less against amphotericin resistant *Candida albicans* and 35% yielding extract minimum inhibitory concentration (MIC) values of 25 micrograms/ml or less against vancomycin resistant *Enterococcus faecium*.

Thin layer chromatography and liquid chromatography/mass spectrometric analyses, as well as Repetitive Extragenic Palindrome Polymerase Chain Reaction (REP-PCR), indicate considerable strain to strain chemical and genetic diversity. Bioassay-guided fractionation of one active extract has led to the isolation of a novel series of metabolites that includes a potent cytotoxin (IC$^{50}$=10 ng/ml against the HCT-116 human colon carcinoma cell line) that has been named salinosporamide A (FIG. 1). This molecule is most closely related to clasto-lactacystin beta-lactone (also called omuralide), the intermediary hydrolysis product of lactacystin, an anti-microbial product. *Salinospora* mide A represents the first natural product to be discovered that possesses a fused beta-lactone gamma-lactam bicyclic ring and is a highly potent anticancer agent.

Figure 2:
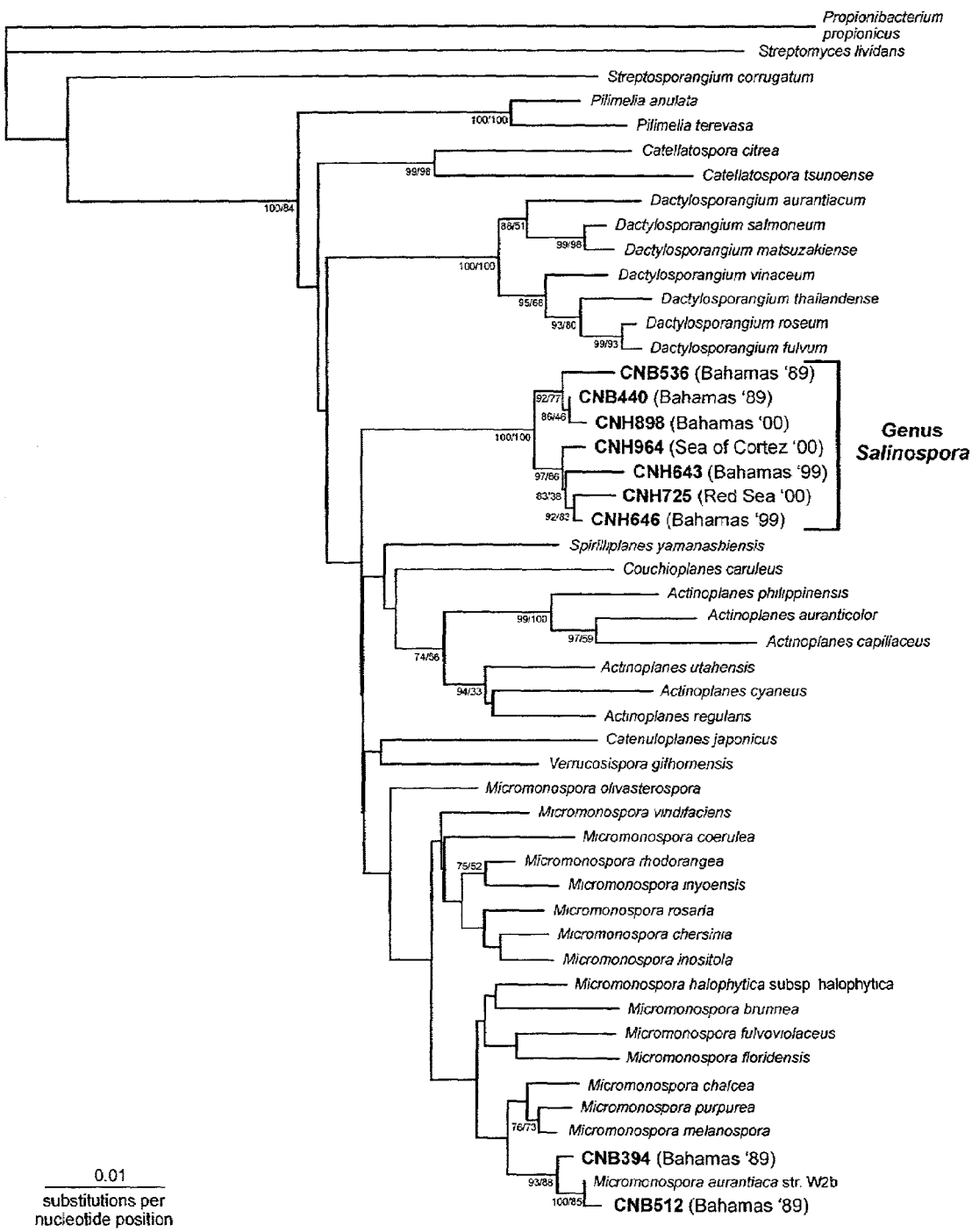
FIG. 2. Phylogenetic dendogram created using the neighbor joining method showing seven diverse members of the *Salinospora* clade along with representatives from all genera officially belonging to the Micromonosporaceae family (Koch, et al; 1996). The distance bar indicates 1 nucleotide substitution per 100 nucleotides. The *Salinospora* clade is shown in the bracket. In parenthesis along side of the *Salinospora* strain designations are the locations and dates of the expeditions from which the isolates were obtained. The *Salinospora* group to date includes 400–500 isolates that showed the characteristic features 1 and 3 (listed in the Background section). These strains are from three expeditions that were grouped first by location and date obtained, then by morphological diversity within each group. From each of these sub-groups, isolates were chosen for almost complete 16S rRNA gene sequencing (greater than 95% of the gene). Phylogenetic programs contained in the Phylip and Clustal W packages were used for analysis and the tree was drawn using Treeview 1.6.1.

The *Salinospora* group was initially recognized after phylogenetic characterization of sediment-derived actinomycetes isolated during an expedition to the Bahamas. Partial 16S rDNA gene sequences from eight morphologically diverse strains indicated the presence of four signature nucleotides between positions 198 to 1424 of SEQ ID NOs: 3, 4 and 5, or nucleotide positions 207–468 (based on the *E. coli* 16S rRNA numbering system which is well known to those skilled in the art; see also Table 3 which utilizes the *E. coli* 16S rRNA numbering system in comparing the *Salinospora* actinomycetes of the present invention to those of other Micromonosporaceae genera). These signatures nucleotides have subsequently been found in all 45 partially sequenced *Salinospora* strains. Two strains showing the highest phylogenetic diversity (CNH643 and CNH646) were sequenced nearly in their entirety (GenBank accession numbers AY040619 (SEQ ID NO:3) and AY040620 (SEQ ID NO:4), respectively) and found to possess one additional signature nucleotide (position 1456) that is also characteristic of this group (Table 3). Phylogenetic analyses of aligned sequences from these strains indicate that they form a distinct and coherent clade within the Micromonosporaceae (FIG. 2). Signature nucleotides unify this clade and a high bootstrap value supports clear separation from the nine currently described genera within the family. SEQ ID NOs: 3 and 4 are identical seQuences. SEQ ID NO:4 is derived from strain CNH646, which was deposited Sep. 27, 2000 (ATCC No. PTA-2501).

16S rRNA signature nucleotides. 16S rRNA signature nucleotides for the genus *Salinospora* and all nine currently accepted genera within the Micromonosporaceae are shown in Table 3. Forty-five diverse *Salinospora* isolates were partially sequenced and confirmed to have all four signature nucleotides at positions 207–468. The signature nucleotide at position 1456 was discovered after subsequent 3' sequencing of the 16S rRNA gene from several (20) *Salinospora* isolates. These are original signatures observed in this study (in addition to those previously published by Koch et al. 1996) that define the coherence of the *Salinospora* clade and separate it from other members of the family. Signature nucleotides were aligned to E. coli positions 27–1492 using all existing members of the Micromonosporaceae in the Ribosomal Database Project. Members of the genus Salinospora show closest homology to Micromonospora olivasterospora (97.1–97.7% similarity), the most deeply rooted member of that genus, with whom they share eight of 12 previously published signature nucleotide positions. Thus Salinospora strains are more highly diverged from their closest phylogenetic neighbor than the recently described genus Verrucosispora gifomensis which shows 98.0% similarity to Micromonospora olivasterospora and shares 11 of 12 previously published signature nucleotides.

TABLE 3

| Relative Nucleotide Position of E. coli 16S RNA | All Other Micormonosporaceae Genera | Salinospora Isolates | Nucleotide Positions of SEQ ID NOs: 4 and 5 |
|---|---|---|---|
| 207 | (U/C) | A | 198 |
| 366 | (A/G) | C | 351 |
| 467 | (A/G) | U | 442 |
| 468 | A | U | 443 |
| 1456 | A | G | 1423 |

A follow-up study was undertaken in the Bahamas to determine the persistence of the Salinospora group. From 20 samples collected from four transects (0–30 m), 355 actinomycetes were observed and over 90% of these displayed characteristic Salinospora morphologies suggesting that this group may be the numerically dominant actinomycete in marine sediments. Of those observed, 100 strains were isolated for further study. The average numbers of Salinospora colony-forming units (cfu's) ranged from $1.2-2.3\times10^3$ cfu's/ml sediment. Over 50% of the Salinospora isolates appeared on a low nutrient medium (M4) indicating the importance of using appropriate isolation techniques. Thirteen representatives of eight different colony morphotypes were partially sequenced and the most phylogenetically diverse isolate (CNH898) was sequenced nearly in its entirety (GenBank Accession number AY040622) (SEQ ID NO:5). Strain CNH898 was deposited Jun. 30, 2003 (ATCC No. PTA-5275).

An examination of 30 actinomycetes with Salinospora morphological characteristics that were isolated from the Bahamas in 1989 (Jensen et al, 1991) revealed that all but two of these strains had an obligate requirement of seawater ($Na^+$) for growth. Ten seawater requiring strains representing six different morphotypes were partially sequenced and found to possess the five Salinospora signature nucleotides between positions 207–468 (Table 3). The nearly complete 16S rDNA sequence of two of these (CNB440 and CNB536, Gen Bank Accession numbers AY040617 (SEQ ID NO:6) and AY040618 (SEQ ID NO:7), respectively) indicates that they are diverse members of the Salinospora clade (FIG. 2). Thus, strains belonging to this new taxon have been isolated from near-shore Bahamian sediments on three separate occasions over an 11-year period indicating that they are persistent members of the sediment bacterial community.

The two strains that did not require seawater for growth (CNB394 and CNB512) but had colony morphologies similar to Salinospora were found to lack the Salinospora signatures in Table 3. Analyses of the almost complete 16S rDNA sequence of these strains showed 99.6–99.9% similarity to Micromonospora aurantiaca str. W2b and the presence of all of the signature nucleotides previously published for the genus Micromonospora (Koch et al, 1996). The phylogenetic dendogram clearly shows that CNB394 and CNB512 are members of the genus Micromonospora (FIG. 2). Micromonospora isolates have been reported from marine sediments (Takizawa et al, 1993), including deep-sea samples (Weyland, 1981), however, unlike Salinospora, this genus is well known from terrestrial soils and seawater-requiring strains have not been reported.

From extended supra-littoral transects (10 locations, 30 samples) made in the Bahamas (2000 expedition), over 1000 actinomycete colonies were observed including low numbers of Micromonosporaceae (ca. 2%), however none of these required seawater for growth. The inability to recover Salinospora strains from supra-littoral samples supports the observation that these bacteria are restricted to the marine environment.

To determine if Salinospora members had a broader distribution, sediments were collected from the Red Sea and the Sea of Cortez. From 42 Red Sea sediment samples, 22 isolates with Salinospora morphologies and an obligate requirement of seawater for growth were obtained. Six isolates representing 4 major morphotypes were partially sequenced and the almost complete 16S rDNA sequence of one strain (CNH725, GenBank Accession number AY040621 (SEQ ID NO:8) is represented in FIG. 3. From 36 sediments collected in the Sea of Cortez, 20 seawater-requiring actinomycete strains were isolated and all of these possessed Salinospora morphological characteristics. Eight strains representing five different morphotypes were partially sequenced and the phylogenetically diverse isolate CNH964 (GenBank Accession number AY040623 (SEQ ID NO:9) was sequenced almost in its entirety. These results clearly indicate that Salinospora members are widely distributed in marine sediments.

Phylogenetic analyses and physiological characteristics indicate that the Salinospora clade represents a new genus within the family Micromonosporaceae. Although it is unlikely that the diversity within this genus has been revealed in the present study, intra-group 16SrDNA sequence similarity (98.6%) and a robust clade topology indicate that this genus is comprised of multiple species (FIG. 2). Placement of the genus Salinospora within the family Micromonosporaceae is supported by the presence of a complete set of family-specific 16S rDNA signature nucleotides (Stackelbrandt, 1997).

Despite evidence that actinomycetes can be recovered from deep-ocean sediments, only one marine species has been described (Helmke and Weyland, 1984) and the inclusion of this group within the autochthonous marine microbiota has not been widely accepted (Bull et al., 2000). Our data provide the first conclusive evidence for the widespread and persistent occurrence in marine sediments of unique populations of obligate marine actinomycetes. Phylogenetic and physiological evidence indicate that these actinomycetes comprise a new taxon and the generic epithet Salinospora gen. nov. has been proposed. Salinospora strains are a prolific source of biologically active secondary metabolites that are useful for a variety of applications.

EXAMPLE 1

Sample collection and bacterial isolation. Samples of the top 1 cm of sediment were collected by SCUBA and processed by either stamping, dilution and heat-shock or both methods. Dilution and heat-shock was carried out as follows: 1 ml of wet sediment was added to 4 ml of sterile seawater, heated for six minutes at 55° C., shaken vigorously, and dilutions of $10^{-2}$ to $10^{-4}$ were inoculated onto agar media (M1–M4). For stamping, 10 ml of wet sediment were aseptically placed into a sterile aluminum dish, dried (ca. 24 hours) in a laminar flow hood, ground lightly with a pestle, pressed into a sterile foam plug (14 mm in diameter) and inoculated onto agar media (M1–M4) by stamping 8–9 times in a clockwise fashion giving a serial dilution effect. All isolation media were prepared with 100% filtered natural seawater. Actinomycetes generally appeared after 4–6 weeks of incubation at 25–28° C. and were considered as any colony with a tough leathery texture, dry or folded appearance and branching filaments with or without aerial mycelia. All isolation media had final concentrations of 100 micrograms/ml cycloheximide and 5 micrograms/ml rifampicin added after autoclaving.

Media were prepared by methods well known to those skilled in the art and all contain seawater. Recipes for media are as follows: M1: 10 grams starch, 4 grams yeast extract, 2 grams peptone, 18 grams agar, 1 liter natural seawater; M2: 6 ml glycerol, 1 gram arginine, 1 gram $K_2HPO_4$, 0.5 grams $MgSO_4$, 18 grams agar, 1 liter natural seawater; M3: 6 grams glucose, 2 grams solubilized chitin, 18 grams agar, 1 liter natural seawater; M4: 2 grams solubilized chitin, 18 grams agar, 1 liter natural seawater; M5: 18 grams agar, 1 liter natural seawater.

EXAMPLE 2

DNA purification, amplification, sequencing and plylogenetic analyses. Genomic DNA was prepared as follows: 10 mg of vegetative mycelia grown on M1 agar for 2–4 weeks at 25–28° C. was macerated and an aqueous cleared lysate, created by standard methods, was precipitated with 0.7 volumes of isopropanol. The resultant DNA pellet was then washed with 70% ethanol and resuspended in 10 mM Tris buffer (pH 8.5) to a final concentration of 100 ng/ml. 16S rDNA sequencing templates were amplified from 10–50 ng of genomic DNA template by the PCR using the primers FC27 (5' AGAGTTTGATCCTGGCTCAG) (SEQ ID 1) and RC1492 (5' TACGGCTACCTTGTTACGACTT) (SEQ ID 2). PCR products were purified with a Qiagen QiAquick PCR clean-up kit using the manufacture's protocols. Partial sequences of morphologically diverse strains were obtained from nucleotides 80–480 (E. coli numbering system) using the FC27 primer. Select 16S rDNA amplicons were sequenced almost in their entirety on both top and bottom strands using a total often primers. The ten contigs were then assembled yielding gene sequences of 1479 to 1483 unambiguous nucleotides. Hypervariable regions in the 16S rDNA sequences were excluded yielding a total of 1408 aligned nucleotides. 16S rDNA similarity values were calculated by the RDP similarity matrix online analysis and compared to the three nearest neighbors in the RDP database. Sequences were aligned to the secondary structure of members of the Micromonosporaceae in the RDP (Maidak et al, 2001) using the BioEdit software (Hall, 1999). Phylogenetic analyses were performed using the neighbor-joining and parsimony based algorithms in the Clustal W software and PHYLIP software packages, respectively (Thompson et al., 1994; Felsenstein, 1993). The dendogram (FIG. 2) was drawn using Treeview 1.6.1 (Page, 1996).

EXAMPLE 3

Genetic-analysis by Repetitive Extragenic Palindromic Polymerase Chain Reaction (REP-PCR). The genetic diversity of Salinospora strains was analyzed using REP-PCR (Versalovic et al., 1991). This technique, when applied to the Salinospora group, involves the use of total genomic DNA as a template and PCR primers specific for repetitive sequences present in the genomes of high G+C content Gram-positive bacteria. The length of the PCR products for any one strain will vary with the position of the repetitive sequences in the genome and result in a population of amplicons of various lengths that when separated on an agarose gel create strain-specific banding patterns. This high throughput method allows for the detection of genetically distinct strains and is more sensitive than 16S rRNA gene analyses as a method to assess genetic diversity. REP-PCR banding patterns are used to sort strains into distinct groups that can produce different gene products. Grouping of strains based on REP-PCR banding patterns correlate well with groups based on the production of secondary metabolites.

EXAMPLE 4

Production and isolation of useful products. Salinospora strains were cultured in multiple sea-water based media including M1 and CKA (starch 5 g, fish hydro-solubles 4 ml, menhaden meal 2 g, kelp powder 2 g, chitosan 2 g, seawater 1 L). An adsorbent resin (XAD-16) was added to the fermentation 24 hours prior to harvest (day 11). The resin was collected by filtration, rinsed with deionized water, and eluted with acetone. Alternatively, cells were collected by filtration, freeze dried and extracted with acetone. The extract was concentrated by rotary evaporation and the residue subjected to C-18 flash chromatography followed by HPLC. The structures of novel fermentation products were resolved using a variety of methods including one- and two-dimensional NMR and mass spectroscopy.

EXAMPLE 5

Antibacterial assay. Extracts from cultured Salinospora strains were tested using standard methods to demonstrate their antibiotic activity against Gram-positive and Gram-negative bacteria. The method used to test against Staphylococcus aureus is detailed below. Similar methods are used to test for antimicrobial activity against other organisms. Extracts were compared to known antibiotics and relative activity levels determined. Extracts with potent antibiotic activity were further analyzed for the presence of novel metabolites.

Briefly, cultures of S. aureus were grown overnight to stationary phase. The number of bacteria per ml was calculated and a uniform number of bacteria were plated into individual wells containing fresh media. Compounds of interest, including known antibiotic agents (e.g. Oxacillin in DMSO at 0.04 mg/mL), were added to a single row of wells and serially diluted down the plate to determine the concentration required to kill the bacteria. Plates were incubated overnight at 37° C. to allow for cell growth. Samples were read in an automated plate reader at 600 nm and MIC concentrations were determined.

EXAMPLE 6

Antifungal assay. Extracts from cultured Salinospora strains were tested using standard methods to demonstrate antifungal activity against Candida albicans. Extracts were compared to known antibiotics and their relative activities determined. Extracts with potent antifungal activity were further analyzed for the presence of novel metabolites.

Briefly, a culture of *C. albicans* was grown overnight to stationary phase. The number of cells per ml was calculated and the suspension was diluted and added to individual wells of 96-well plates. Alamar blue was added to each well as an indicator of viability. Test extracts were added to a single row of wells and serially diluted down the plate to determine the concentration required to kill the fungal cells. Known antifungal agents such as amphotericin were used as a control. Plates were incubated for 12–15 hours at 37° C. Cell concentrations were determined using an automated plate reader at 600 nm and MIC concentrations were determined.

EXAMPLE 7

Assay for the inhibition of growth of colon carcinoma cells and of ovarian cancer cells in vitro. The cytotoxicity of extracts from cells or culture media were assessed in vitro against the human colon carcinoma cell line HCT116 and the human ovarian carcinoma cell line A2780 by MTS assay. Cells were plated at 4,000 cells per well in 96 well microliter plates and, after 24 hours, the extract (dissolved in DMSO or other appropriate solvent) was added and serially diluted. The cells were incubated with the compound at 37° C. for 72 hours, then the tetrazolium dye MTS was added to a final concentration of 333 μg/ml and the electron coupling agent phenazine methosulfate was added to a final concentration of 25 μM. Once reduced, MTS is converted into a water insoluble blue crystal formazan and that was read at an absorbance at 490 nm with a microplate reader. As dead cells are unable to reduce MTS, the amount of formazan is correlated to the number of viable cells. The $IC_{50}$, the drug concentration required to inhibit proliferation of 50% of the cells, was used as a measure of efficacy.

EXAMPLE 8

Anti-Herpes Simplex Virus (HSV-1) assay. Antiviral activity can also be determined using an MTS assay. Vero cells were plated into duplicate 96-well plates for infection with virus and cytotoxicity control. One plate of cells was incubated with virus for an hour at 37° C. Both plates were overlaid with a series of concentrations of the extract of interest and plates were incubated for five days. MTS solution was added to the plates and the plates were incubated for three hours as described above. Absorbance at 490 nm was read with a microplate reader and correlated to antiviral activity and cellular toxicity.

EXAMPLE 9

Chemical mutagenesis of *Salinospora* strains to generate overproducing strains. Chemical mutagenesis of *Salinospora* strains can be performed to generate strains that overproduce a desired product. For example, a strain that produces an antibiotic at a low level is treated with ethylmethylsulfonate (EMS) during the mid-log growth phase. Mutagenized cultures are streaked onto plates to allow for the isolation of individual clones. From the individual clones, cultures are grown and the antibiotic, in a crude or pure form, is isolated. The relative yields of the compounds of interest produced by the mutagenized strains are compared to the original strain to select an overproducing strain.

EXAMPLE 10

Heterologous gene expression. Actinomycete strains have been useful as hosts for the production of secondary metabolites from other more slowly growing organisms (Tang, et al., 2000). Genes, either singly or in clusters, can be expressed in *Salinospora* strains for the production of proteins or secondary metabolites. Methods for transferring nucleic acids into bacteria are well known by those skilled in the art.

EXAMPLE 11

Gene cluster isolation and expression. The synthesis of a number of actinmycete antibiotics (e.g. actinorhodin, frenolicin, granaticin, griseusin, octatetracycline, and tetracenomycin) are produced by clustered polyketide synthetase (PKS) genes (Hopwood, 1995). PKS genes are classified into two types of large mutifunctional proteins. In PKS type I genes, the substrate progresses through a number of active sites on a single protein. In PKS type II genes, multiprotein complexes are produced and the substrate progresses from one protein to the next. PKS type II genes have been cloned and expressed in heterologous systems, either in their native groupings or in novel combinations. Combining genes for the synthesis of secondary metabolites from *Salinospora* with genes from other actinomycetes provides a novel method of biologically assisted combinatorial chemistry that can lead to the production of novel small molecules. Also, *Salinospora* biosynthetic genes can be shuffled and expressed in an heterologous host leading to the production of new metabolites. PKS genes are not the only ones that occur in modules. For example, non-ribosomal peptide synthetases are modular as well, and are frequently present in the actinomycetes. Biosynthetic gene clusters from the novel *Salinospora* group can be used as genetic feedstock for the expression of novel molecules in heterologous strains or for the over-production of native and recombinant gene products.

EXAMPLE 12

Assay for anti-inflammatory activity. Extracts from *Salinospora* cultures are tested by measuring inhibition of phorbol-induced inflammation (edema) in a mouse ear assays. This is a conventional test which has been accepted as demonstrating a compound's effectiveness in reducing inflammation. The compound is topically applied in acetone to the inside pinnae of the ears of mice in a solution containing an edema-causing irritant, i.e. phorbol 12-myristate 13-acetate (PMA). PMA alone (2 microgram per ear) or in combination with varying amounts of the extract is applied to the left ear (5 mice per treatment group) while an acetone (control) is applied to the right. After a 3-hour and 20-minute incubation at 23° C., the mice are sacrificed, the ears removed, and bores taken and weighed. Edema is measured by subtracting the weight of the right ear (control) from the weight of the left ear (treatment). The results are recorded as a percent decrease (inhibition) or percent increase (potentiation) in edema relative to PMA.

EXAMPLE 13

Enzyme inhibition assay. Extracts from *Salinospora* strains could be tested for their ability to inhibit enzyme activity. Extracts could be prepared as described above and serial dilutions of the extract added to enzyme-substrate mixtures to determine an $IC_{50}$ for the reaction.

EXAMPLE 14

Enzyme activity assay. Assays for enzyme activity can be tested by growing *Salinospora* strains in the presence of substrates of interest including, but not limited to chitin, lignin, cellulose, and other recalcitrant biopolymers, etc. Depending on the substrate, assays can be performed to determine the amount of substrate remaining or the amount of product produced.

EXAMPLE 15

Agriculture/aquaculture protection assay. Assays for the protection of plants from pathogens and general growth enhancement can be performed in a standard greenhouse trial. The strain of interest can be applied to the plant directly or incorporated into the growth media. Plants could be challenged by subjecting them to a pathogen and comparing their growth to control groups treated with a pathogen alone, treated with a *Salinospora* strain alone, or untreated. Rates of growth could be compared to select for strains with the desired activities.

Although an exemplary embodiment of the invention has been described above by way of example only, it will be understood by those skilled in the field that modifications may be made to the disclosed embodiment without departing from the scope of the invention, which is defined by the appended claims.

REFERENCES

Bull, A. T., A. C. Ward, and M. Goodfellow. 2000. Search and discovery strategies for biotechnology: The paradigm shift. *Microbiology and Molecular Biology Reviews.* 64:573–606.

Felsenstein, J. PHYLIP (Phylogeny Inference Package) version 3.5c. (Distributed by the author. Department of Genetics, University of Washington, Seattle., 1993).

Goodfellow, M., and J. A. Haynes. 1984. Actinomycetes in marine sediments, p. 453-472. In L. Ortiz-Ortiz, L. F. Bojalil, and V. Yakoleff (ed.), Biological, biochemical, and biomedical aspects of actinomycetes. Academic Press, Inc. Orlando.

Goodfellow M. and S. T. Williams. 1983. Ecology of actinomycetes. *Ann. Rev. Microbiol.* 37:189–216.

Helmke, E. and Weyland, H. 1984. *Rhodococcus marinonascens* sp. nov., an actinomycete from the Sea. *Int. J. Syst. Bacteriol.* 34:127–38.

Hopwood, D. A. 1995. Genetic manipulation of Streptomyces polyketide synthase genes for novel secondary metabolite production. *FEMS Microbiol. Rev.* 16:233–4.

Jensen, P. R., Dwight, R., and Fenical, W. 1991. Distribution of actinomycetes in near-shore tropical marine sediments. *Appl. Environ. Microbiol* 57:1102–8.

Koch, C., R. M. Kroppenstedt, F. A. Rainey, and E. Stackebrandt. 1996. 16S ribosomal DNA analysis of the genera *Micromonospora, Actinoplanes, Catellatospora, Catenuloplanes, Couchioplanes, Dactylosporangium,* and *Pilimelia* and emendation of the family Micromonosporaceae. International Journal of Systematic Bacteriology. 46:765–768.

Page, R. D. M. 1996. TREEVIEW: An application to display phylogenetic trees on personal computers. *Computer Applications in the Biosciences* 12, 357–358.

Stackebrandt, E., F. A. Rainey, and N. L. Ward-Rainey. 1997. Proposal for a new hierarchic classification system, Actinobacteria classis nov. *International Journal of Systematic Bacteriology.* 47:479–491.

Takizawa, M., Colwell, R. R. & Hill, R. T. 1993. Isolation and diversity of actinomycetes in the Chesapeake Bay. *Applied and Environmental Microbiology* 59, 997–1002.

Tang, L., Shah, S., Chung, L., Carney, J., Katz, L., Khosla, C., and Julien, B. 2000. Cloning and heterologous expression of the epothilong gene cluster. *Science.* 287:640–2.

Thompson, J. D., Higgins, D. G. & Gibson, T. J. 1994. CLUSTAL W: Improving the sensitivity of progressive multiple sequence alignment through sequence weighting, position-specific gap penalties and weight matrix choice. *Nucleic Acids Research* 22:4673–4680.

Versalovic, J., T. Koeuth, and J. R. Lupski. 1991. Distribution of repetitive DNA sequences in eubacteria and application to fingerprinting of bacterial genomes. *Nucleic Acids Res.* 19:6823–6831.

Weyland, H. 1981. Distribution of actinomycetes on the sea floor. *Actinomycetes, Zbl. Bakt. Suppl.* 11:185–193.

---

SEQUENCE LISTING

```
<160> NUMBER OF SEQ ID NOS: 2

<210> SEQ ID NO 1
<211> LENGTH: 20
<212> TYPE: DNA
<213> ORGANISM: Escherichia coli

<400> SEQUENCE: 1
agagtttgat cctggctcag                                          20

<210> SEQ ID NO 2
<211> LENGTH: 22
<212> TYPE: DNA
<213> ORGANISM: Escherichia coli

<400> SEQUENCE: 2
tacggctacc ttgttacgac tt                                       22
```

We claim:

1. An isolated marine actinomycete having an obligate requirement of sodium for growth, wherein the marine actinomycete is a strain of *Salinospora* comprising 16S rRNAs SEQ ID NO:4 or 5.

2. The strain of *Salinospora* of claim 1, wherein the strain of *Salinospora* is obtained from sediment.

3. The isolated strain of *Salinospora* of claim 1, wherein SEQ ID NOs:4 or 5 have signature nucleotides not found in other Micromonosporaceae 16S rRNAs.

4. The isolated strain of *Salinospora* of claim 3, wherein the signature nucleotides are numbered and identified in accordance to the *E.coli* 16S rRNA sequence, wherein a uridine or cytosine at position 207 is an adenosine; an adenosine or guanine at position 366 is a cytosine; an adenosine or guanine at position 467 is a uracil; an adenosine at position 468 is a uracil; and adenosine at position 1456 is a guanine.

5. The method for producing a biomolecule, comprising
   culturing a strain of *Salinospora* of claim 1 in a sodium containing growth media, wherein the biomolecule is produced by the strain of *Salinospora*;
   collecting the strain of *Salinospora* or the sodium containing growth media containing the biomolecule; and
   extracting the biomolecule from the strain of *Salinospora* or the sodium containing growth media, thereby producing the biomolecule.

6. The method of claim 5, wherein the growth media comprises sodium at a concentration of 450 mM.

7. An isolated strain of *Salinospora* having an obligate requirement of sodium for growth, wherein the strain of *Salinospora* is a strain of *Salinospora* comprising 16S rRNAs SEQ ID NO:4 or 5 and signature nucleotides therein, wherein the signature nucleotides are numbered and identified in accordance to the *E.coli* 16S rRNA sequence, wherein a uridine or cytosine at position 207 is an adenosine; an adenosine or guanine at position 366 is a cytosine; an adenosine or guanine at position 467 is a uracil; an adenosine at position 468 is a uracil; and adenosine at position 1456 is a guanine.

8. An isolated strain of *Salinospora* having an obligate requirement of sodium for growth, wherein the strain of *Salinospora* is a strain of *Salinospora* comprising a 16S rRNA and signature nucleotides therein, wherein the signature nucleotides are numbered and identified in accordance to the *E.coli* 16S rRNA sequence, wherein a uridine or cytosine at position 207 is an adenosine; an adenosine or guanine at position 366 is a cytosine; an adenosine or guanine at position 467 is a uracil; an adenosine at position 468 is a uracil; and adenosine at position 1456 is a guanine.

9. The strain of *Salinospora* of claims 4, 7 or 8, wherein the strain of *Salinospora* is obtained from sediment.

* * * * *

UNITED STATES PATENT AND TRADEMARK OFFICE
CERTIFICATE OF CORRECTION

| | | |
|---|---|---|
| PATENT NO. | : 7,144,723 B2 | Page 1 of 15 |
| APPLICATION NO. | : 09/991518 | |
| DATED | : December 5, 2006 | |
| INVENTOR(S) | : Fenical et al. | |

It is certified that error appears in the above-identified patent and that said Letters Patent is hereby corrected as shown below:

Following columns 13 and 14, delete the entire Sequence Listing and replace with the Sequence Listing as follows:

```
                          SEQUENCE LISTING

<160>  NUMBER OF SEQ ID NOS: 9

<210>  SEQ ID NO 1
<211>  LENGTH: 20
<212>  TYPE: DNA
<213>  ORGANISM: Artificial sequence <223>  Amplification primer <400>  SEQUENCE: 1
       agagtttgat cctggctcag                                         20

<210>  SEQ ID NO 2
<211>  LENGTH: 22
<212>  TYPE: DNA
<213>  ORGANISM: Artificial sequence <223>  Amplification primer <400>  SEQUENCE: 2
       tacggctacc ttgttacgac tt                                      22
```

UNITED STATES PATENT AND TRADEMARK OFFICE
CERTIFICATE OF CORRECTION

PATENT NO. : 7,144,723 B2
APPLICATION NO. : 09/991518
DATED : December 5, 2006
INVENTOR(S) : Fenical et al.

It is certified that error appears in the above-identified patent and that said Letters Patent is hereby corrected as shown below:

```
<210>  SEQ ID NO 3
<211>  LENGTH: 1479
<212>  TYPE: DNA
<213>  ORGANISM: Salinospora sp. CNH643 16S ribosomal RNA gene, partial sequence <400>  SEQUENCE: 3
       agagtttgat cctggctcag gacgaacgct ggcggcgtgc ttaacacatg caagtcgagc    60
       ggaaaggccc ttcggggtac tcgagcggcg aacgggtgag taacacgtga gtaacctgcc   120
       ccaggctttg gataacccc gggaaaccgg ggctaatacc ggatatgacc atctgtcgca   180
       tggtgggtgg tggaaagatt ttttggcttg ggatgggctc gcggcctatc agcttgttgg   240
       tggggtgatg gcctaccaag gcggcgacgg gtagccggcc tgagagggcg accggccaca   300
       ctgggactga gacacggccc agactcctac gggaggcagc agtggggaat cttgcacaat   360
       gggcggaagc ctgatgcagc gacgccgcgt gagggatgac ggccttcggg ttgtaaacct   420
       ctttcagcag gacgaagcg tttgtgacgg tacctgcaga agaagcgccg gccaactacg   480
       tgccagcagc cgcggtaaga cgtagggcgc aagcgttgtc cggatttatt gggcgtaaag   540
       agctcgtagg cggcttgtcg cgtcgactgt gaaaacccgt ggctcaactg cgggcttgca   600
       gtcgatacgg gcaggctaga gttcggtagg ggagactgga attcctggtg tagcggtgaa   660
       atgcgcagat atcaggagga acaccggtgg cgaaggcggg tctctgggcc gatactgacg   720
```

UNITED STATES PATENT AND TRADEMARK OFFICE
CERTIFICATE OF CORRECTION

PATENT NO.        : 7,144,723 B2
APPLICATION NO. : 09/991518
DATED             : December 5, 2006
INVENTOR(S)       : Fenical et al.

It is certified that error appears in the above-identified patent and that said Letters Patent is hereby corrected as shown below:

```
ctgaggagcg aaagcgtggg gagcgaacag gattagatac cctggtagtc cacgctgtaa    780
acgttgggcg ctaggtgtgg ggggcctctc cggttctctg tgccgcagct aacgcattaa    840
gcgccccgcc tggggagtac ggccgcaagg ctaaaactca aaggaattga cggggcccg     900 cacaagcggc ggagcatgcg gattaattcg atgcaacgcg aagaacctta cctgggtttg    960
acatcgccgg aaatccttca gagatggggg gtccttcggg gccggtgaca ggtggtgcat   1020
ggctgtcgtc agctcgtgtc gtgagatgtt gggttaagtc ccgcaacgag cgcaaccctt   1080
gttcgatgtt gccagcgcgt tatggcgggg actcatcgaa gactgccggg gtcaactcgg   1140
aggaaggtgg ggatgacgtc aagtcatcat gccccttatg tccagggctt cacgcatgct   1200
acaatggccg gtacagtggg ctgcgatacc gtgaggtgga gcgaatccca aaaagccggt   1260
ctcagttcgg atcggggtct gcaactcgac cccgtgaagt cggagtcgct agtaatcgca   1320
gatcagcaac gctgcggtga atacgttccc gggccttgta cacaccgccc gtcacgtcac   1380
gaaagtcggc aacacccgaa gccggtggcc taaccttgt gggggagcc gtcgaaggtg     1440 gggctggcga ttgggacgaa gtcgtaacaa ggtagccgt                          1479
```

UNITED STATES PATENT AND TRADEMARK OFFICE
CERTIFICATE OF CORRECTION

PATENT NO.         : 7,144,723 B2
APPLICATION NO.    : 09/991518
DATED              : December 5, 2006
INVENTOR(S)        : Fenical et al.

It is certified that error appears in the above-identified patent and that said Letters Patent is hereby corrected as shown below:

```
<210>  SEQ ID NO 4
<211>  LENGTH: 1479
<212>  TYPE: DNA
<213>  ORGANISM: Salinospora sp. CNH646 16S ribosomal RNA gene, partial sequence <400>  SEQUENCE: 4
       agagtttgat cctggctcag gacgaacgct ggcggcgtgc ttaacacatg caagtcgagc    60
       ggaaaggccc ttcggggtac tcgagcggcg aacgggtgag taacacgtga gtaacctgcc   120
       ccaggctttg ggataacccc gggaaaccgg ggctaatacc ggatatgacc atctgtcgca   180
       tggtgggtgg tggaaagatt ttttggcttg ggatgggctc gcggcctatc agcttgttgg   240
       tggggtgatg gcctaccaag gcggcgacgg gtagccggcc tgagagggcg accggccaca   300
       ctgggactga gacacggccc agactcctac gggaggcagc agtggggaat cttgcacaat   360
       gggcggaagc ctgatgcagc gacgccgcgt gagggatgac ggccttcggg ttgtaaacct   420
       ctttcagcag ggacgaagcg tttgtgacgg tacctgcaga agaagcgccg gccaactacg   480
       tgccagcagc cgcggtaaga cgtagggcgc aagcgttgtc cggatttatt gggcgtaaag   540
       agctcgtagg cggcttgtcg cgtcgactgt gaaaacccgt ggctcaactg cgggcttgca   600
       gtcgatacgg gcaggctaga gttcggtagg ggagactgga attcctggtg tagcggtgaa   660
       atgcgcagat atcaggagga acaccggtgg cgaaggcggg tctctgggcc gatactgacg   720
```

UNITED STATES PATENT AND TRADEMARK OFFICE
CERTIFICATE OF CORRECTION

PATENT NO. : 7,144,723 B2 Page 5 of 15
APPLICATION NO. : 09/991518
DATED : December 5, 2006
INVENTOR(S) : Fenical et al.

It is certified that error appears in the above-identified patent and that said Letters Patent is hereby corrected as shown below:

```
ctgaggagcg aaagcgtggg gagcgaacag gattagatac cctggtagtc cacgctgtaa    780
acgttgggcg ctaggtgtgg ggggcctctc cggttctctg tgccgcagct aacgcattaa    840
gcgccccgcc tggggagtac ggccgcaagg ctaaaactca aaggaattga cggggggcccg   900 cacaagcggc ggagcatgcg gattaattcg atgcaacgcg aagaaccttacctgggtttg    960 acatcgccgg aaatccttca gagatggggg gtccttcggg gccggtgaca ggtggtgcat   1020
ggctgtcgtc agctcgtgtc gtgagatgtt gggttaagtc ccgcaacgag cgcaacccctt  1080 gttcgatgtt gccagcgcgt tatggcgggg actcatcgaa gactgccggg gtcaactcgg   1140
aggaaggtgg ggatgacgtc aagtcatcat gccccttatg tccagggctt cacgcatgct   1200
acaatggccg gtacagtggg ctgcgatacc gtgaggtgga gcgaatccca aaaagccggt   1260
ctcagttcgg atcggggtct gcaactcgac cccgtgaagt cggagtcgct agtaatcgca   1320
gatcagcaac gctgcggtga atacgttccc gggccttgta cacaccgccc gtcacgtcac   1380
gaaagtcggc aacacccgaa gccggtggcc taaccttgt gggggggagcc gtcgaaggtg   1440 gggctggcga ttgggacgaa gtcgtaacaa ggtagccgt                          1479
```

UNITED STATES PATENT AND TRADEMARK OFFICE
CERTIFICATE OF CORRECTION

PATENT NO. : 7,144,723 B2
APPLICATION NO. : 09/991518
DATED : December 5, 2006
INVENTOR(S) : Fenical et al.

It is certified that error appears in the above-identified patent and that said Letters Patent is hereby corrected as shown below:

```
<210>  SEQ ID NO 5
<211>  LENGTH: 1479
<212>  TYPE: DNA
<213>  ORGANISM: Salinospora sp. CNH898 16S ribosomal RNA gene, partial sequence <400>  SEQUENCE: 5
       agagtttgat cctggctcag gacgaacgct ggcggcgtgc ttaacacatg caagtcgagc    60
ggaaaggccc ttcggggtac tcgagcggcg aacgggtgag taacacgtga gtaacctgcc   120
ccaggctttg ggataacccc gggaaaccgg ggctaatacc ggatatgact ggctgccgca   180
tggtggttgg tggaaagatt ttttggcttg ggatgggctc gcggcctatc agcttgttgg   240
tggggtgatg gcctaccaag gcggcgacgg gtagccggcc tgagagggcg accggccaca   300
ctgggactga gacacggccc agactcctac gggaggcagc agtggggaat cttgcacaat   360
gggcggaagc ctgatgcagc gacgccgcgt gagggatgac ggccttcggg ttgtaaacct   420
ctttcagcag ggacgaagcg tttgtgacgg tacctgcaga agaagcgccg gccaactacg   480
tgccagcagc cgcggtaaga cgtagggcgc aagcgttgtc cggatttatt gggcgtaaag   540
agctcgtagg cggcttgtcg cgtcgactgt gaaaacccgt ggctcaactg cgggcttgca   600
gtcgatacgg gcaggctaga gttcggtagg ggagactgga attcctggtg tagcggtgaa   660
atgcgcagat atcaggagga acaccggtgg cgaaggcggg tctctgggcc gatactgacg   720
```

UNITED STATES PATENT AND TRADEMARK OFFICE
CERTIFICATE OF CORRECTION

PATENT NO.        : 7,144,723 B2
APPLICATION NO. : 09/991518
DATED             : December 5, 2006
INVENTOR(S)       : Fenical et al.

It is certified that error appears in the above-identified patent and that said Letters Patent is hereby corrected as shown below:

```
ctgaggagcg aaagcgtggg gagcgaacag gattagatac cctggtagtc cacgctgtaa    780
acgttgggcg ctaggtgtgg ggagcctctc cggttctctg tgccgcagct aacgcattaa    840
gcgccccgcc tggggagtac ggccgcaagg ctaaaactca aggaattga cggggggcccg    900 cacaagcggc ggagcatgcg gattaattcg atgcaacgcg aagaaccta cctgggtttg     960 acatcgccgg aaatccttca gagatggggg gtccttcggg gccggtgaca ggtggtgcat   1020
ggctgtcgtc agctcgtgtc gtgagatgtt gggttaagtc ccgcaacgag cgcaacccctt  1080 gttcgatgtt gccagcgcgt tatggcgggg actcatcgaa gactgccggg gtcaactcgg   1140
aggaaggtgg ggatgacgtc aagtcatcat gccccttatg tccagggctt cacgcatgct   1200
acaatggccg gtacaatggg ctgcgatacc gtgaggtgga gcgaatccca aaaagccggt   1260
ctcagttcgg atcggggtct gcaactcgac cccgtgaagt cggagtcgct agtaatcgca   1320
gatcagcaac gctgcggtga atacgttccc gggccttgta cacaccgccc gtcacgtcac   1380
gaaagtcggc aacacccgaa gccggtggcc taaccttgt gggggagcc gtcgaaggtg     1440 gggctggcga ttgggacgaa gtcgtaacaa ggtagccgt                          1479
```

UNITED STATES PATENT AND TRADEMARK OFFICE
CERTIFICATE OF CORRECTION

PATENT NO. : 7,144,723 B2
APPLICATION NO. : 09/991518
DATED : December 5, 2006
INVENTOR(S) : Fenical et al.

It is certified that error appears in the above-identified patent and that said Letters Patent is hereby corrected as shown below:

```
<210>  SEQ ID NO 6
<211>  LENGTH: 1480
<212>  TYPE: DNA
<213>  ORGANISM: Salinospora sp. CNH440 16S ribosomal RNA gene, partial sequence <400>  SEQUENCE: 6
       agagtttgat cctggctcag gacgaacgct ggcggcgtgc ttaacacatg caagtcgagc      60
ggaaaggccc ttcggggtac tcgagcggcg aacgggtgag taacacgtga gtaacctgcc     120
ccaggctttg ggataacccc gggaaaccgg gctaatacc ggatatgact ggctgccgca      180
tggtggttgg tggaaagatt ttttggcttg ggatgggctc gcggcctatc agcttgttgg     240
tggggtgatg gcctaccaag gcggcgacgg gtagccggcc tgagagggcg accggccaca     300
ctgggactga gacacggccc agactcctac gggaggcagc agtggggaat cttgcacaat     360
gggcggaagc ctgatgcagc gacgccgcgt gagggatgac ggccttcggg ttgtaaacct     420
ctttcagcag ggacgaagcg tttgtgacgg tacctgcaga agaagcgccg gccaactacg     480
tgccagcagc cgcggtaaga cgtagggcgc aagcgttgtc cggatttatt gggcgtaaag     540
agctcgtagg cggcttgtcg cgtcgactgt gaaaacccgt ggctcaactg cgggcttgca     600
gtcgatacgg gcaggctaga gttcggtagg ggagactgga attcctggtg tagcggtgaa     660
atgcgcagat atcaggagga acaccggtgg cgaaggcggg tctctgggcc gatactgacg     720
```

Page 8 of 15

UNITED STATES PATENT AND TRADEMARK OFFICE
CERTIFICATE OF CORRECTION

PATENT NO.       : 7,144,723 B2                                Page 9 of 15
APPLICATION NO.  : 09/991518
DATED            : December 5, 2006
INVENTOR(S)      : Fenical et al.

It is certified that error appears in the above-identified patent and that said Letters Patent is hereby corrected as shown below:

```
ctgaggagcg aaagcgtggg gagcgaacag gattagatac cctggtagtc cacgctgtaa    780
acgttgggcg ctaggtgtgg ggagcctctc cggttctctg tgccgcagct aacgcattaa    840
gcgccccgcc tggggagtac ggccgcaagg ctaaaactca aaggaattga cggggcccg     900 cacaagcggc ggagcatgcg gattaattcg atgcaacgcg aagaacctta cctgggtttg    960
acatcgccgg aaatccttca gagatggggg gtccttcggg gccggtgaca ggtggtgcat   1020
ggctgtcgtc agctcgtgtc gtgagatgtt gggttaagtc ccgcaacgag cgcaacccttt 1080 gttcgatgtt gccagcgcgt tatggcgggg actcatcgaa gactgccggg gtcaactcgg  1140
aggaaggtgg ggatgacgtc aagtcatcat gccccttatg tccagggctt cacgcatgct  1200
acaatggccg gtacaatggg ctgcgatacc gtgaggtgga gcgaatccca aaaagccggt  1260
ctcagttcgg atcggggtct gcaactcgac cccgtgaagt cggagtcgct agtaatcgca  1320
gatcagcaac gctgcggtga atacgttccc gggccttgta cacaccgccc gtcacgtcac  1380
gaaagtcggc aacacccgaa gccggtggcc taaccttgt gggggagcc gtcgaaggtg   1440 gggctggcga ttgggacgaa gtcgtaacaa ggtagccgta                        1480
```

UNITED STATES PATENT AND TRADEMARK OFFICE
CERTIFICATE OF CORRECTION

PATENT NO. : 7,144,723 B2
APPLICATION NO. : 09/991518
DATED : December 5, 2006
INVENTOR(S) : Fenical et al.

Page 10 of 15

It is certified that error appears in the above-identified patent and that said Letters Patent is hereby corrected as shown below:

```
<210>  SEQ ID NO 7
<211>  LENGTH: 1479
<212>  TYPE: DNA
<213>  ORGANISM: Salinospora sp. CNH536 16S ribosomal RNA gene, partial sequence <400>  SEQUENCE: 7
       agagtttgat cctggctcag gacgaacgct ggcggcgtgc ttaacacatg caagtcgagc     60
ggaaaggccc ttcggggtac tcgagcggcg aacgggtgag taacacgtga gtaacctgcc    120
ccaggctttg ggataacccc gggaaaccgg ggctaatacc ggatatgact ggctgccgca    180
tggtggttgg tggaaagatt ttttggcttg ggatgggctc gcggcctatc agcttgttgg    240
tggggtgatg gcctaccaag gcggcgacgg gtagccggcc tgagagggcg accggccaca    300
ctgggactga gacacggccc agactcctac gggaggcagc agtggggaat cttgcacaat    360
gggcggaagc ctgatgcagc gacgccgcgt gagggatgac ggccttcggg ttgtaaacct    420
ctttcagcag ggacgaagcg tttgtgacgg tacctgcaga agaagcgccg gccaactacg    480
tgccagcagc cgcggtaaga cgtagggcgc aagcgttgtc cggatttatt gggcgtaaag    540
agctcgtagg cggcttgtcg cgtcgactgt gaaaacccgt ggctcaactg cgggcttgca    600
gtcgatacgg gcaggctaga gttcggtagg ggagactgga attcctggtg tagcggtgaa    660
atgcgcagat atcaggagga acaccggtgg cgaaggcggg tctctgggcc gatactgacg    720
```

UNITED STATES PATENT AND TRADEMARK OFFICE
CERTIFICATE OF CORRECTION

PATENT NO.         : 7,144,723 B2                                Page 11 of 15
APPLICATION NO. : 09/991518
DATED              : December 5, 2006
INVENTOR(S)      : Fenical et al.

It is certified that error appears in the above-identified patent and that said Letters Patent is hereby corrected as shown below:

```
ctgaggagcg aaagcgtggg gagcgaacag gattagatac cctggtagtc cacgctgtaa   780
acgttgggcg ctaggtgtgg ggagcctctc cggttctctg tgccgcagct aacgcattaa   840
gcgccccgcc tggggagtac ggccgcaagg ctaaaactca aaggaattga cgggggcccg   900
cacaagcggc ggagcatgcg gattaattcg atgcaacgcg aagaacctta cctgggtttg   960
acatcgccgg aaatccttca gagatggggg gtccttcggg gccggtgaca ggtggtgcat  1020
ggctgtcgtc agctcgtgtc gtgagatgtt gggttaagtc ccgcaacgag cgcaaccctt  1080
gttcgatgtt gccagcgcgt tatggcgggg actcatcgaa gactgccggg gtcaactcgg  1140
aggaaggtgg ggatgacgtc aagtcatcat gccccttatg tccagggctt cacgcatgct  1200
acaatggccg gtacaatggg ctgcgatacc gtgaggtgga gcgaatccca aaaagccggt  1260
ctcagttcgg atcggggtct gcaactcgac cccgtgaagt cggagtcgct agtaatcgca  1320
gatcagcaac gctgcggtga atacgttccc gggccttgta cacaccgccc gtcacgtcac  1380
gaaagtcggc aacacccgaa gccggtggcc taacccttgt gggggagcc gtcgaaggtg   1440 gggctggcga ttgggacgaa gtcgtaacaa ggtagccgt                         1479
```

UNITED STATES PATENT AND TRADEMARK OFFICE
CERTIFICATE OF CORRECTION

PATENT NO. : 7,144,723 B2
APPLICATION NO. : 09/991518
DATED : December 5, 2006
INVENTOR(S) : Fenical et al.

It is certified that error appears in the above-identified patent and that said Letters Patent is hereby corrected as shown below:

```
<210>  SEQ ID NO 8
<211>  LENGTH: 1479
<212>  TYPE: DNA
<213>  ORGANISM: Salinospora sp. CNH725 16S ribosomal RNA gene, partial sequence <400>  SEQUENCE: 8
       agagtttgat cctggctcag gacgaacgct ggcggcgtgc ttaacacatg caagtcgagc    60
ggaaaggccc ttcggggtac tcgagcggcg aacgggtgag taacacgtga gtaacctgcc   120
ccaggctttg ggataacccc gggaaaccgg ggctaatacc ggatatgacc atctgtcgca   180
tggtgggtgg tggaaagatt ttttggcttg ggatgggctc gcggcctatc agcttgttgg   240
tggggtgatg gcctaccaag gcggcgacgg gtagccggcc tgagagggcg accggccaca   300
ctgggactga gacacggccc agactcctac gggaggcagc agtggggaat cttgcacaat   360
gggcggaagc ctgatgcagc gacgccgcgt gagggatgac ggccttcggg ttgtaaacct   420
ctttcagcag ggacgaagcg tttgtgacgg tacctgcaga agaagcgccg gccaactacg   480
tgccagcagc cgcggtaaga cgtagggcgc aagcgttgtc cggatttatt gggcgtaaag   540
agctcgtagg cggcttgtcg cgtcgactgt gaaaaccgt ggctcaactg cgggcttgca    600
gtcgatacgg gcaggctaga gttcggtagg ggagactgga attcctggtg tagcggtgaa   660
atgcgcagat atcaggagga acaccggtgg cgaaggcggg tctctgggcc gatactgacg   720
```

UNITED STATES PATENT AND TRADEMARK OFFICE
CERTIFICATE OF CORRECTION

PATENT NO. : 7,144,723 B2
APPLICATION NO. : 09/991518
DATED : December 5, 2006
INVENTOR(S) : Fenical et al.

It is certified that error appears in the above-identified patent and that said Letters Patent is hereby corrected as shown below:

```
ctgaggagcg aaagcgtggg gagcgaacag gattagatac cctggtagtc cacgctgtaa    780
acgttgggcg ctaggtgtgg ggggcctctc cggttctctg tgccgcagct aacgcattaa    840
gcgccccgcc tggggagtac ggccgcaagg ctaaaactca aaggaattga cggggcccg    900 cacaagcggc ggagcatgcg gattaattcg atgcaacgcg aagaacctta cctgggtttg    960
acatcgccgg aaatccttca gagatggggg gtccttcggg gccggtgaca ggtggtgcat    1020
ggctgtcgtc agctcgtgtc gtgagatgtt gggttaagtc ccgcaacgag cgcaacccttt   1080 gttcgatgtt gccagcgcgt tatggcgggg actcatcgaa gactgccggg gtcaactcgg    1140
aggaaggtgg ggatgacgtc aagtcatcat gccccttatg tccagggctt cacgcatgct    1200
acaatggccg gtacagtggg ctgcgatacc gtgaggtgga gcgaatccca aaaagccggt    1260
ctcagttcgg atcggggtct gcaactcgac cccgtgaagt cggagtcgct agtaatcgca    1320
gatcagcaac gctgcggtga atacgttccc gggccttgta cacaccgccc gtcacgtcac    1380
gaaagtcggc aacacccgaa gccggtggcc taaccttgt gggggagcc gtcgaaggtg    1440 gggctggcga ttgggacgaa gtcgtaacaa ggtagccgt                           1479
```

UNITED STATES PATENT AND TRADEMARK OFFICE
CERTIFICATE OF CORRECTION

PATENT NO. : 7,144,723 B2
APPLICATION NO. : 09/991518
DATED : December 5, 2006
INVENTOR(S) : Fenical et al.

It is certified that error appears in the above-identified patent and that said Letters Patent is hereby corrected as shown below:

```
<210>  SEQ ID NO 9
<211>  LENGTH: 1479
<212>  TYPE: DNA
<213>  ORGANISM: Salinospora sp. CNH964 16S ribosomal RNA gene, partial sequence <400>  SEQUENCE: 9
       agagtttgat cctggctcag gacgaacgct ggcggcgtgc ttaacacatg caagtcgagc    60
       ggaaaggccc ttcggggtac tcgagcggcg aacgggtgag taacacgtga gtaacctgcc   120
       ccaggctttg ggataacccc gggaaaccgg ggctaatacc ggatatgacc atctgtcgca   180
       tggtgggtgg tggaaagatt ttttggcttg ggatgggctc gcggcctatc agcttgttgg   240
       tggggtgatg gcctaccaag gcggcgacgg gtagccggcc tgagagggcg accggccaca   300
       ctgggactga gacacggccc agactcctac gggaggcagc agtggggaat cttgcacaat   360
       gggcggaagc ctgatgcagc gacgccgcgt gagggatgac ggccttcggg ttgtaaacct   420
       ctttcagcag ggacgaagcg tttgtgacgg tacctgcaga agaagcgccg gccaactacg   480
       tgccagcagc cgcggtaaga cgtagggcgc aagcgttgtc cggatttatt gggcgtaaag   540
       agctcgtagg cggcttgtcg cgtcgactgt gaaaacctgt ggctcaactg cgggcttgca   600
       gtcgatacgg gcaggctaga gttcggtagg ggagactgga attcctggtg tagcggtgaa   660
       atgcgcagat atcaggagga acaccggtgg cgaaggcggg tctctgggcc gatactgacg   720
```

Page 14 of 15

UNITED STATES PATENT AND TRADEMARK OFFICE
CERTIFICATE OF CORRECTION

PATENT NO.         : 7,144,723 B2
APPLICATION NO.    : 09/991518
DATED              : December 5, 2006
INVENTOR(S)        : Fenical et al.

It is certified that error appears in the above-identified patent and that said Letters Patent is hereby corrected as shown below:

```
ctgaggagcg aaagcgtggg gagcgaacag gattagatac cctggtagtc cacgctgtaa    780
acgttgggcg ctaggtgtgg ggggcctctc cggttctctg tgccgcagct aacgcattaa    840
gcgccccgcc tggggagtac ggccgcaagg ctaaaactca aaggaattga cgggggcccg    900
cacaagcggc ggagcatgcg gattaattcg atgcaacgcg aagaacctta cctgggtttg    960
acatcgccgg aaatccttca gagatggggg gtccttcggg gccggtgaca ggtggtgcat   1020
ggctgtcgtc agctcgtgtc gtgagatgtt gggttaagtc ccgcaacgag cgcaaccctt   1080
gttcgatgtt gccagcgcgt tatggcgggg actcatcgaa gactgccggg gtcaactcgg   1140
aggaaggtgg ggatgacgtc aagtcatcat gccccttatg tccagggctt cacgcatgct   1200
acaatggccg gtacagtggg ctgcgatacc gtgaggtgga gcgaatccca aaaagccggt   1260
ctcagttcgg atcgggtct gcaactcgac cccgtgaagt cggagtcgct agtaatcgca   1320
gatcagcaac gctgcggtga atacgttccc gggccttgta cacaccgccc gtcacgtcac   1380
gaaagtcggc aacacccgaa gccggtggcc taacccttgt gggggagcc gtcgaaggtg   1440 gggctggcga ttgggacgaa gtcgtaacaa ggtagccgt                           1479
```

Signed and Sealed this

Eighth Day of April, 2008

JON W. DUDAS
*Director of the United States Patent and Trademark Office*